United States Patent [19]
Singleton et al.

[11] Patent Number: 5,507,133
[45] Date of Patent: Apr. 16, 1996

[54] INOCULANT METHOD AND APPARATUS

[75] Inventors: Paul Singleton; Joseph Rourke; Michael Sadowsky, all of Honolulu, Hi.

[73] Assignee: University of Hawaii, Honolulu, Hi.

[21] Appl. No.: 193,394

[22] Filed: Feb. 7, 1994

[51] Int. Cl.$^6$ .............................. A01H 1/00; B65B 29/10; C05F 11/08; C12N 5/00
[52] U.S. Cl. ................... 53/474; 53/239; 53/425
[58] Field of Search .............................. 53/474, 239, 238, 53/445, 425, 426; 206/220, 219, 221; 383/38, 3

[56] References Cited

U.S. PATENT DOCUMENTS

| | | | |
|---|---|---|---|
| 2,925,719 | 2/1960 | Robbins et al. | 53/239 X |
| 3,168,796 | 2/1965 | Scott et al. | |
| 3,184,395 | 5/1965 | Brewer . | |
| 3,314,194 | 4/1967 | Halleck | 47/34.11 |
| 3,320,697 | 5/1967 | Larsen | 47/34.11 |
| 3,323,640 | 6/1967 | Kugler | 206/47 |
| 4,229,544 | 10/1980 | Haynes et al. | 435/253 |
| 4,463,522 | 8/1984 | Lindemann | 47/58 |
| 4,631,905 | 12/1986 | Maloney | 53/239 X |
| 4,632,244 | 12/1986 | Landau | 53/474 X |
| 4,769,945 | 9/1988 | Motoyama et al. | 47/57.6 |
| 4,849,005 | 7/1989 | Williams et al. | 71/7 |
| 4,875,921 | 10/1989 | Paau | 71/7 |
| 4,908,315 | 3/1990 | Kertz | 435/240.4 |
| 4,999,301 | 3/1991 | Bryan-Jones | 435/252.5 |
| 5,061,490 | 10/1991 | Paau et al. | 424/93 |
| 5,171,683 | 12/1992 | Kertz | 435/240.4 |
| 5,207,320 | 5/1993 | Allen | 53/474 X |
| 5,398,483 | 3/1995 | Smith et al. | 53/474 |

FOREIGN PATENT DOCUMENTS 9015527  12/1990  WIPO .

OTHER PUBLICATIONS

FAO production Yearbook, Various years.
Frost et al., Use of Microorganisms in Agriculture will Triple in Europe in Four Years. Research Studies (1990), via DIALOG Database No. 16 PTS Promt.
NifTAL Project and Mircen. Annual Report 1991.
Papadoulos, Biotechnica About to Begin Field Trails and Regulatory Issues in Biotechnology, Drexel Burnham Lambert Inc. Biotechnology Monthly. via DIALOG Data-Base No. 545 INVESTEXT Report No. 705779 (1987).
Roskoski, Joann P. Biological Nitrogen Fixation (BNF): Commonly asked questions and answers. Illustrated Concepts in Agricultural Biotechnology. No. 4. A series from the NifTAL Project-MIRCEN, Dept. of Agronomy and Soil Science, College of Tropical Agriculture and Human Resources, University of Hawaii (1989).
Singleton et al. Legume Response to Rhizobial Inoculation in the Tropics; Miths and Realities. in Myths and Science of Soil of the Tropics. SSSA (Soil Science Society of America) Special Publication No. 29 (1992).

(List continued on next page.)

*Primary Examiner*—James F. Coan
*Attorney, Agent, or Firm*—James Creighton Wray

[57] ABSTRACT

A unique package for inoculants and a method for enabling the end user to introduce a pure culture of a microorganism into its appropriate growth substance, and later the microorganism enriched substance into a carrier material within a self-contained unit. The basic package separates a stabilized pure culture of the microorganism from the growth substance by a clamp which forms a physical partition. The microorganism is introduced to the substance when the partition is eliminated. After a time of growth to a maximum extent possible in the substance, the package is fractured to release the fresh inoculation at maximum microorganism vitality. Growth of the microorganism in the growth substance in-situ results in maximum numbers of the beneficial microorganism being available at the site of application.

18 Claims, 2 Drawing Sheets

OTHER PUBLICATIONS

Wheat et al., Biotechnology in Agriculture—Industry Report. Arthur D. Little Decision Resources, Inc. via DIALOG Database No. 545 INVESTEXT Report No. 1118580 (1988).

Biotechnology in Agriculture: The Next Decade; Nitrogen Fixation. Research Studies—Decisions Resources Inc. Feb. 1992. via DIALOG Database no. 16 PTS Promt.

NIFTAL, Biological Nitrogen Fixation. BNF Bulletin. Winter/Spring 1992. vol. XI (1).

INOCULANT METHOD AND APPARATUS

BACKGROUND OF THE INVENTION

The present invention relates to an improved apparatus and method for packaging, storing, producing and combining inoculants and components thereof. More particularly this invention relates to a new and improved apparatus and method for avoiding loss of product quality due to adverse conditions which affect living microorganisms contained in commercial inoculant products.

The present invention may be used in any situation requiring the application of high numbers of microorganisms including, but not limited to agriculture (horticulture, floriculture, field crop production, forestry, animal husbandry), aquaculture, terrestrial and marine ecological remediation bio-degradation systems, and fermented food industry.

The use of legume inoculants offers both economic and environmental advantages because it reduces the dependence on chemical fertilizers. Also, use of inoculants can increase the yield of legumes specifically alfalfa by as much as 15%. For other legumes, the Rhizobial inoculants currently available increase the yield from no less than 10% to more than 200%. In addition, introduction of Rhizobia by seed inoculation is simple, inexpensive, and energy efficient.

The market for nitrogen-fixing microbial inoculants is about $15 million in the United States, about 25% of which is inoculant for alfalfa, clovers, and other forage legumes. The market is rather stable, with the number of acres treated declining, but with the decrease being compensated by more purchases of higher-priced inoculants. Based on some assumptions made it has been estimated that the value of the inoculant market would have increased to about $40 million (1988 dollars) in the United States by 1995. Worldwide sales would have been at least $80 million by that time (Wheat, D. W. et al, 1988, Biotechnology in Agriculture—Industry Report, Arthur D. Little Decision Resources, Inc. via DIALOG Database No. 545 INVESTEXT Report No. 1118580). In Western Europe, Frost and Sullivan estimate that by 1994, the microbial inoculants market is expected to reach $93.7, up from $32.9 million in 1989. (Frost & Sullivan, 1990, Research Studies, "Use of microorganisms in agriculture will triple in Europe in four years." via DIALOG Database No. 16 PTS Promt). The largest application in that market is fermentation of silage, followed by soil inoculants, or the bacteria which fix nitrogen. The primary market opportunities for soil inoculants is seen in Italy and France, where soybean production has increased dramatically. Decision Resources Inc. (1992) presented the potential market for microbial products for the year 2000 as follows:

TABLE 1

| | World: Markets for Microbial Products, 2000 | | | |
|---|---|---|---|---|
| | US ($ mil) | US (%) | WORLD ($ mil) | WORLD (%) |
| Microbial Pesticides | 500–1000 | 83.6–88.1 | 1000–2000 | 83.6–86.9 |
| Silage Inoculants | 70–100 | 11.7–8.8 | 150–200 | 12.3–8.7 |
| Rhizobium Inoculants | 20 | 3.3–1.8 | 50 | 4.11–2.2 |
| Others* | 8–15 | 1.3 | 15–50 | 1.2–2.2 |
| TOTAL | 598–1135 | 100 | 1215–2300 | 100 |

*(Frost & Sullivan, 1990, Id.).

In developed countries such as the USA, Canada, Australia, and some European countries, commercial enterprises based on the inoculant production technology exist at this time. In developing countries however, promotion and use of Rhizobial inoculants and the establishment of an inoculant industry is still in its early stages and would only be successful with the demonstration of its significant benefits (Singleton, Paul W., Bohlool, B. B., and Nakao, P. L. 1992. "Legume response to Rhizobial inoculation in the tropics: myths and realities, in Myths and Science of Soils of the Tropics." Soil Science Society of America, Special Publication no. 29. As the use of legume inoculants become more widespread, market potential also grows. Legumes are an important food source which are grown in different parts of the world.

TABLE 2

| | Soybean Area Harvested, 1985–88 (in 000 Hectares) | | | | | |
|---|---|---|---|---|---|---|
| | WORLD | USA | SOUTH AMERICA | ASIA | EUROPE | AFRICA |
| 1985 | 53089 | 24922 | 14306 | 11155 | 639 | 372 |
| 1986 | 51905 | 23590 | 13245 | 12329 | 763 | 386 |
| 1987 | 52475 | 23057 | 13570 | 12541 | 1105 | 411 |
| 1988 | 54651 | 23222 | 15920 | 12306 | 1025 | 434 |

For soybean alone, there were about 55 million hectares harvested in 1988. Most of the soybean area harvested is in the US, but the Asian and African countries where researchers have done some of their inoculation trials, constitute about a quarter of the total soybean harvest area. At an inoculation rate of 0.3 kilograms inoculant/hectare, Asia and Africa together will require about 3.8 million kilograms of inoculant. That is equivalent to about 42 million 90 gm-bags of peat inoculant.

One of the advantages of using Rhizobial inoculants is that they are more economical compared to petroleum-based nitrogen fertilizers. It has been estimated that it would take at least $87 worth of urea/hectare to produce a soybean yield comparable to that possible using only $3 worth of the inoculant. That would translate to $38 million worth of inoculants in Asia and Africa. If 20% of that market is captured, it would be worth about $7.6 million. In the U.S., although most of the market is geared towards soybeans, only 15% of planted acreage is treated with Rhizobia. Another sector of the US market is the market for alfalfa, which is more stable. Despite being smaller than the soybean market, approximately 80–90% of planted alfalfa acreage is inoculated (Biotechnology in Agriculture: The Next Decade: Nitrogen Fixation, Research Studies—Decision Resources, Inc. February 1992. via DIALOG Database No. 16 PTS Promt).

Rhizobial inoculants for many legume crops are manufactured in a number of countries around the world. Indonesia has Rhizogin-Indonesia; Australia has Agricultural Laboratories; the Philippines has the University of the Philippines at Los Banos, and Zambia has the Mt. Makulu Research Station, as the major inoculant production facilities (BNF Bulletin. Winter/Spring 1992. Vol. XI (1)).

Based solely on legume inoculant market in U.S. estimated revenues generated from legume inoculant product sales are valued at 60–80 million dollars/year. The current international market is 10 times the US market. Based on an understanding of legume-Rhizobia system, quality of inoculant legume products at the farm would be enhanced 10 fold. Conservatively estimated inoculant producers would be willing to pay 10% of their gross product value for the final product that the present invention teaches. Since the difficulty of maintaining viability while shipping microbial inoculants limits U.S. exports, the market growth for these products should be enhanced.

The use of the present invention would result in high cost savings and benefits due to a more cost-effective method of transporting sensitive and fragile microbiological components into adverse environments, which reduces dependency on climate-controlled storage and transportation, and results in consumer savings in cost of application per unit.

The "fermentation" technology for producing pure cultures of Rhizobia is well developed. Inoculants either are applied to the legume seed in bulk before planting, are used in a granular form as a soil treatment, or are sprayed on the soil. After reaching maximum numbers in growth vessels, pure broth cultures of Rhizobia are then mixed with a carrier material to produce the final inoculant product. One of the conventional methods involves mixing the legume seeds with the appropriate strain of the Rhizobium before planting and is usually carried out in the open environment.

The current industry standards in preparing inoculants are the sterile and non sterile "carrier" techniques. The sterile technique may use a diluted culture of the appropriate microorganism and a carrier material (e.g. peat) which has been sterilized either by irradiation or by steaming. The diluted culture is injected into the bag containing the sterile carrier. By massaging the bag and mixing the culture with the carrier, the microorganism can regrow up to the pre dilution concentration within 5–7 days.

The non sterile technique requires a concentrated pure broth culture of the microorganism for the non sterilized carrier. The sterile technique has the advantage of producing more inoculant from the same amount of pure culture produced through "fermentation," more organisms per unit weight inoculant, and a longer shelf life. This is made possible by the use of a diluted culture instead of a pure culture.

A limitation associated with inoculation success or failure is that it is highly site-specific. It would depend on the interaction of multitude environmental and management variables such as soil nitrogen availability, indigenous Rhizobia, soil, climate, crop history and other interrelated factors. Another limitation is that, although it is beneficial in newly planted fields, its benefits may be limited in major legume-growing regions due to the presence of larger competing indigenous Rhizobial populations.

Commercial inoculant products contain living microorganisms which are sensitive to adverse conditions associated with transportation and storage. All microbial inoculants have a finite shelf-life affecting product quality in transit to markets. Population decline of microbial inoculant with time and under existing conditions of heat and desiccation is well documented. In effect, product quality is highest shortly after production.

A need exists for an inoculant packaging system which provides adequate protection against product quality decline due to factors encountered by transportation and storage age.

SUMMARY OF THE INVENTION

The "dilution" concept embodied in the present invention is in contrast to the conventional method which produces the desired number of microorganisms through fermentation at the production site. The "dilution" concept embodied in the invention makes it possible to grow the microorganisms in situ and, therefore, reduces quality loss, which has been the case with the conventional method. As an extension of the "dilution" concept, it is also possible to rejuvenate a pure culture of microorganism whose quality or the number of viable microorganisms has been significantly diminished as a result of transport and other adverse environmental conditions.

This invention mediates the problem of viability loss and decreased product quality between production and end use, that is common to all inoculants.

In general, the present invention provides a unique package which enables the end user to introduce a pure culture of a microorganism into its appropriate growth substrate within a self-contained unit.

An object of the present invention is to provide a packaging system with plural individual compartments, separated by physical partitions.

Another object of the present invention is to provide a packaging system which separates a stabilized pure culture of a microorganism from a growth substrate by a physical partition.

Another object of the present invention is to provide for a packaging system with means to grow the microorganism in the substrate in-situ to achieve maximum numbers of the beneficial microorganism being available at the site of application.

Still another object of the present invention is to avoid loss of product quality due to adverse conditions. When microorganisms are introduced into an appropriate sterile substrate and environment, they grow to a maximum population density peculiar to the organism and substrate. As long as a minimum number of organisms survive as a starter culture for introduction into the substrate, high product quality can be achieved.

In a preferred embodiment of the invention, the package is constructed of a single unit having a physical partition. The partition forms two compartments, which separately contain a pure culture of a suitable microorganism, and a growth substrate for the microorganism, such as sterile peat. Each component is physically separated by the partition. The partition is eliminated at a specific stage of the production process.

Another object of the present invention is to lessen the use of fermentors because more inoculant can be produced with the same amount of pure culture. The invention saves on time and money, because the use of fermentors in larger scale production can require a major investment for introducing inoculant culture. The invention also saves time and money, because quality loss during transportation and during exposure to harsh conditions is minimized. The use of the right strain or combination of strains of Rhizobium, as well as the pre-packaged amount, help ensure that the benefits derived from inoculation are maximized.

These and further and other objects and features of the invention are apparent in the disclosure, which includes the above and ongoing written specification, with the claims and the drawings.

DETAILED DESCRIPTION OF THE DRAWINGS

Figure 1:
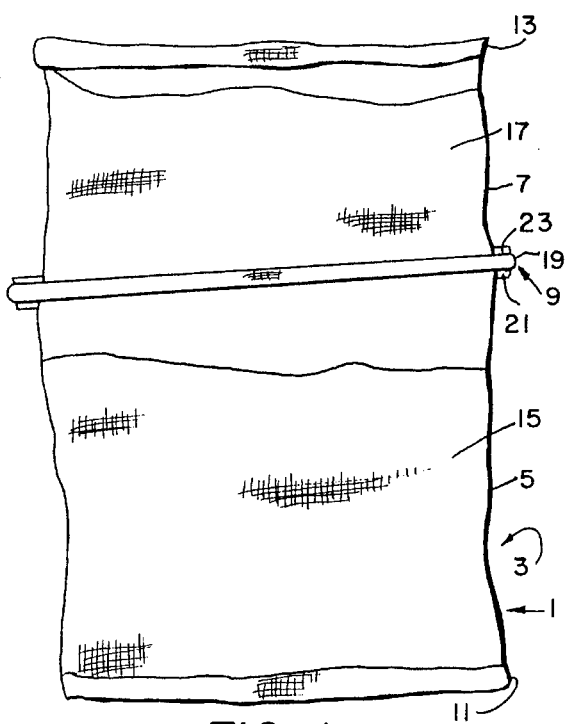
FIG. 1 shows a bag with two compartments, one filled with sterilized peat, and the other filled with inoculant.

Referring to the drawings, the new product within the package is generally referred to by the numeral 1. The package is a bag 3 which is divided into first and second compartments 5 and 7 by a clamp, generally indicated by the numeral 9. Bag 3 is a tube sealed at its lower end 11 by a usual thermo-sealing process. The bag is also sealed at its top edge 13 by a conventional heat sealing. In the upper compartment 7 is a biological product 15, which is a microorganism. In the lower compartment 5 is a substance 15 which affects the biological product 17 within the package. The substance 15 and the biological product 17 are held separately until shortly before the biological product is used. In the present invention, the biological product is a Rhizobial inoculant that is used to treat seeds of legumes to obtain maximum benefits from nitrogen fixation. Populations of the microorganisms decrease during storage and shipment, and especially after exposure to elevated temperatures. The present packaging makes it possible to rejuvenate the inoculant to its original strength before use. For example, after exposure to 45° C., populations may fall from about $10^9$ per grams of inoculant to $10^3$. It is possible to rejuvenate the inoculant to $10^9$ per gram with the packaging of the present invention.

In one example of the invention, the invention is used for the inoculation of legume seeds. In one example, the biological product is legume seed which has been treated with Rhizobia, and the substance affecting the biological product is legume inoculant culture.

Figure 2:
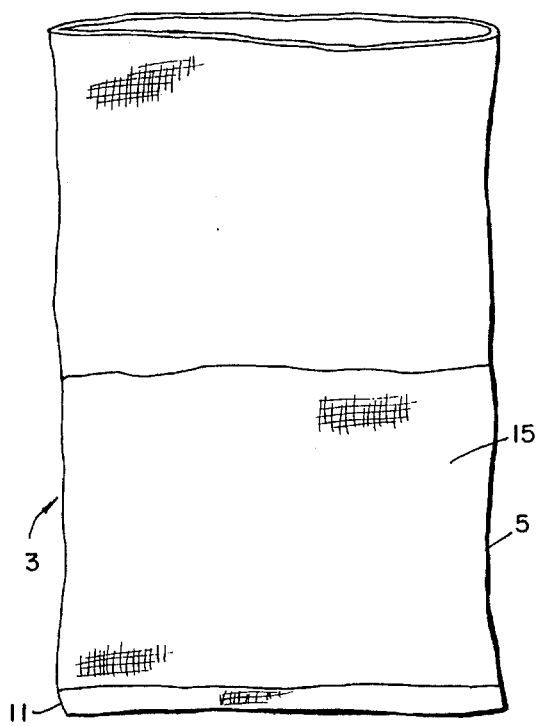
FIG. 2 shows a bag filled with peat.

As shown in FIG. 2, the bag 3 is made of a continuous plastic tube, which is sealed at one end 11.

The substance, in this case sterile peat 15, is added to the sealed end of the bag.

Figure 3:
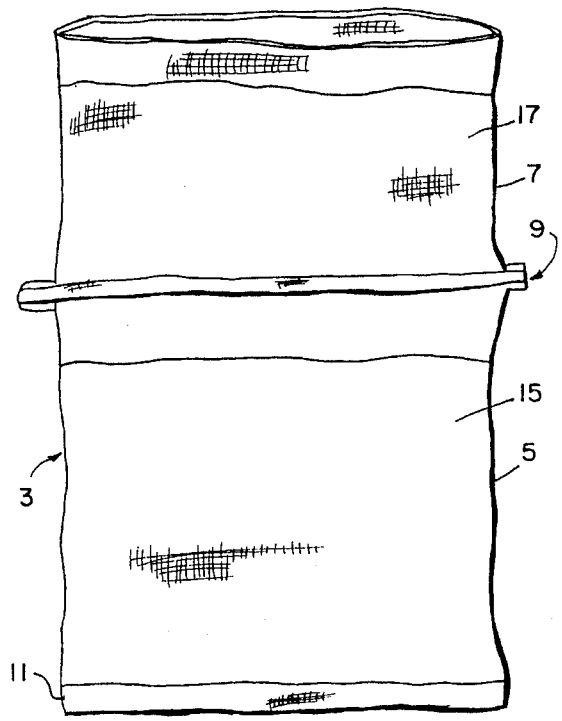
FIG. 3 shows a bag filled with peat and clamped to form a second compartment which is filled with inoculant before sealing.
Figure 4:
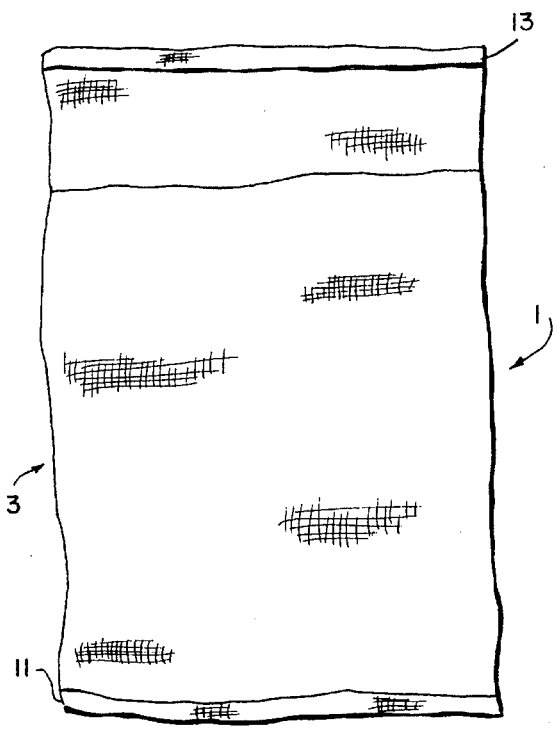
FIG. 4 shows the bag from which the clamp has been removed to mix the inoculant and the peat before using the inoculant.

As shown in FIG. 3, the bag is clamped with a clamp 9 above the sterile peat 15 in the first compartment 5.

Then the entire bag and its contents may be again sterilized, such as by irradiating the bag and its contents.

As shown in FIG. 3, the biological product 17 is then added to the upper compartment 7. In this case, the biological product may be peat which has been inoculated with microorganisms and which has a population of about $10^9$ microorganisms per gram.

Figure 5:
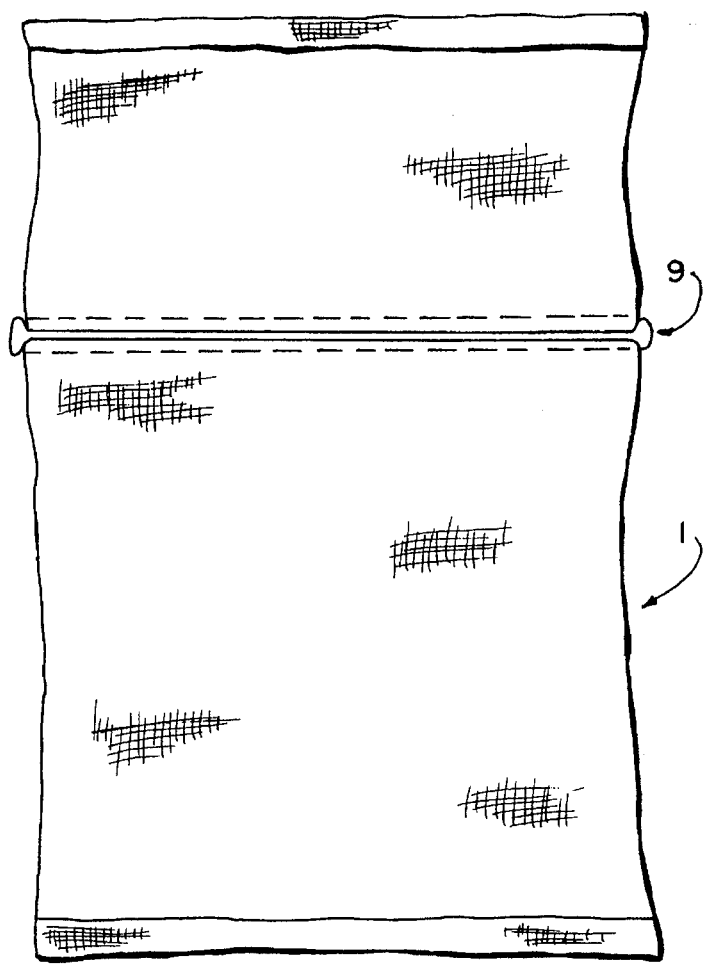
FIG. 5 is a shipping and storing configuration of the product.
Figure 6:
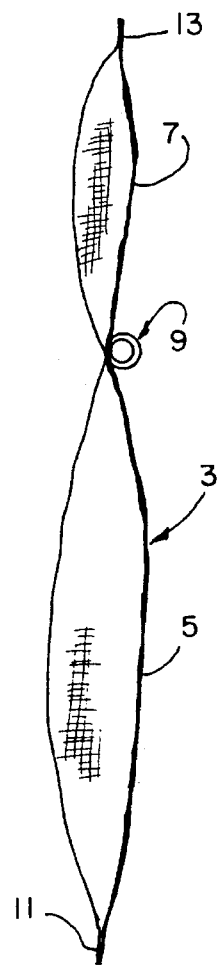
FIG. 6 is a side view of the product shown in FIG. 5.

Then the upper edge 13 of the bag is sealed, such as with a heated iron or a thermal sealing unit, taking care to avoid raising the temperature of the inoculated biological product 17. The sealed package takes the configuration as shown in FIGS. 1, 5 and 6. The product is shipped and stored until just before use, when the clamp is removed and the biological product 17 in the upper compartment 7 is mixed with the fresh sterile peat substance 15 in a lower compartment 5, which rejuvenates the inoculant to about $10^9$ microorganisms per gram.

Finally, the package is opened and the peat which contains the rejuvenated inoculant is mixed with legume seeds to inoculate the seeds with the Rhizobia microorganisms prior to planting the seed.

Figure 7:
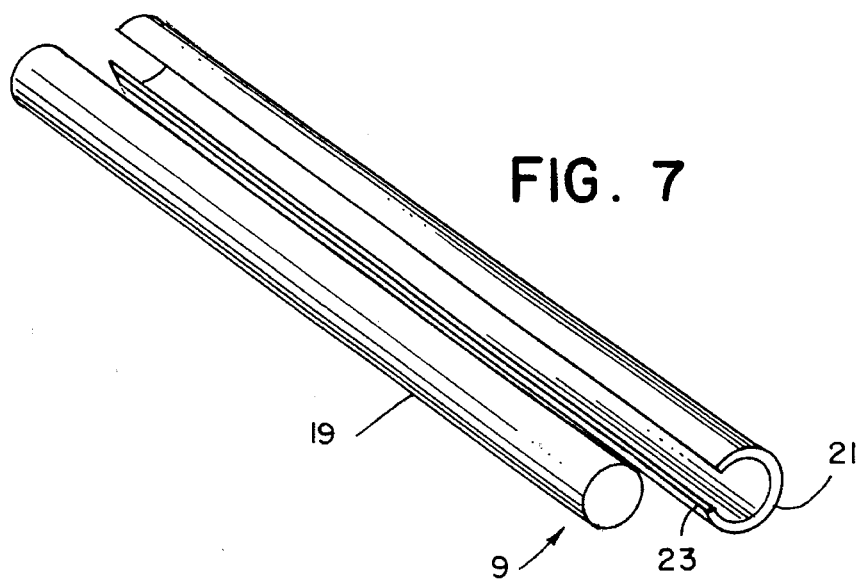
FIG. 7 is a detail of the clamp.

In one form, as shown in FIGS. 6 and 7, the clamp 9 is made of a dowel 19 surrounded by a long plastic tube 21, which is slit 23 and into which the dowel 19 is forced. The slit tube 21 clamps upon the dowel 19 with a portion of the bag intermediate the dowel and interior of the tube 21. The clamp 9 thus prevents the peat from migrating between the compartments 15 and 17 until the clamp 9 is removed.

The invention uses only one membrane formed in a continuous tube, which is eventually sealed at both ends and which uses an external mechanical device to separate the biological product from the substance that affects the biological product.

The invention is a one-membrane package physically divided into at least two compartments by a clip or clamp.

The invention incorporates the "dilution" concept, which makes it possible to grow the number of desired microorganisms just by adding sterile peat to the inoculant, which contains a smaller number of microorganisms.

The present invention is contrasted to a conventional method, which might produce the desired number of microorganisms through fermentation at the production site. In the present invention, the microorganisms are grown in situ. The invention reduces quality loss which has occurred with conventional methods.

Using the invention, it is possible to rejuvenate a pure culture of microorganisms whose quality or number of viable microorganisms have been significantly diminished as a result of transportation and adverse environmental conditions. Since the invention requires a less concentrated culture, a smaller amount of microorganism is necessary to produce the inoculant. The invention makes it possible to preserve the quality of legume inoculants during transportation from the production site of the microorganism to the inoculation and planning site.

The culture and the carrier material will then be thoroughly mixed together to a uniform distribution. The newly prepared inoculant will be incubated for a second time period to achieve the highest cell density possible to the inoculant.

The inoculant may then be used in part or in its entirety from the package. Because of the extremely high numbers of effective viable cells present in the packaged inoculant, the product is potentially capable of producing a greater effect than currently produced inoculants in less than ideal working conditions. Both systems would have been subjected to the same conditions of transportation and storage to arrive at the site of application. Because the elements of conventional packaging systems are not stabilized as the components of the present invention are, there is a higher degree of product quality loss in the conventional system as compared to the present invention. Storage and shelf life of conventional systems are far less. The new package system is not subject of loss of viability or quality until the components are combined to produce the active product. The package and method of the present invention allow inoculants produced for various legume crops to be conveyed to remote areas in one shipment. One inoculant package may be used while others are held in storage, awaiting activation to produce fresh inoculants at the sowing of the next crops.

While the invention has been described with reference to specific embodiments, modifications and variations of the invention may be constructed without departing from the scope of the invention, which is defined in the following claims.

We claim:

1. An inoculant packaging and production system comprising an air tight one-membrane package having a physical partition, wherein said partition and the one membrane package form individual first and second compartments, which separately receive a culture of a suitable microorganism and a growth substance for said microorganism.

2. The apparatus of claim 1, wherein said physical partition is a removable clamp for isolating each component until removal of the clamp.

3. The apparatus of claim 1, wherein the substance material is subjected to preliminary physical and chemical preparatory processes, before being loaded and sealed into the first compartment.

4. The apparatus of claim 1, wherein the substance is a sterile peat.

5. The apparatus of claim 1, wherein the package is sterilized by cobalt 60 gamma-irradiation at a dosage of 5.0 mRads, before the pure culture of a microorganism is placed into the first compartment and sealed in the package.

6. The apparatus of claim 1, wherein the pure culture of the microorganism is in a stabilized form of low metabolic activity for achieving long periods of storage time and tolerance to adverse conditions.

7. The apparatus of claim 1, wherein activation of the system is accomplished by removing a clamp and thereby removing the physical partition between the first compartment containing microorganism and the second compartment containing growth substance, followed by intermingling the pure microorganism and the growth supporting substance.

8. The apparatus of claim 7, wherein the dormant microorganism is stimulated to an active growing state when introduced into the growth substance for achieving a maximum cell density in the growth substance after a period of incubation.

9. The apparatus of claim 1, wherein a dilution process is activated when the culture of the microorganism is released into the growth substance by removing and clamp and shaking and inverting the unit for intermingling the growth substance of the microorganism.

10. The apparatus of claim 1, wherein the culture and the growth substance are mixed together to a uniform distribution, resulting in an inoculant, wherein said inoculant is incubated for a certain period, for achieving the highest cell density possible of the inoculant.

11. A method for packaging precursor elements and producing inoculant, comprising forming an air tight one-membrane package having a physical partition, forming by said partition and the package first and second compartments separately storing, a pure culture of a suitable microorganism, and a growth substance for said microorganism, and a carrier in the respective compartments.

12. The method of claim 11, wherein the storing further comprises separating the growth substance from the pure culture of the suitable microorganism by the first partition which is a clamp for isolating the pure culture from the growth substance.

13. The method of claim 12, wherein the storing further comprises separating the growth substance and the pure culture.

14. The method of claim 11, wherein the growth substance is loaded and sealed into the second compartment, after having been subject to physical and chemical preparatory processes.

15. The method of claim 11, wherein the growth substance is loaded and sealed into the second compartment, and subsequently the system package is sterilized by cobalt 60 gamma-irradiation at a dosage of 5.0 mRads.

16. The method of claim 15, wherein the pure culture of a microorganism is stabilized with low metabolic activity for achieving a long period of storage time and tolerance to adverse conditions and is loaded and sealed into the first compartment.

17. The method of claim 11, further comprising activating the system by removing a clamp and thereby removing the partition between the first and the second compartments, and shaking, kneading and inverting the package, and mixing the pure culture and the growth substance.

18. The method of claim 17, further comprising stimulating growth of the microorganism when the growth substance is mixed with the pure culture, achieving a maximum cell density of the microorganism after a period of incubation in the growth substance.

* * * * *